United States Patent
Guzman

(10) Patent No.: US 7,153,407 B2
(45) Date of Patent: Dec. 26, 2006

(54) MULTI-DIMENSIONAL ELECTROPHORESIS APPARATUS

(75) Inventor: Norberto A. Guzman, East Brunswick, NJ (US)

(73) Assignee: Princeton Biochemicals, Inc., Princeton, NJ (US)

(*) Notice: Subject to any disclaimer, the term of this patent is extended or adjusted under 35 U.S.C. 154(b) by 377 days.

(21) Appl. No.: 10/821,328

(22) Filed: Jun. 17, 2002

(65) Prior Publication Data

US 2004/0226822 A1    Nov. 18, 2004

Related U.S. Application Data

(63) Continuation of application No. 09/436,186, filed on Nov. 8, 1999, now Pat. No. 6,406,604.

(51) Int. Cl.
*G01N 27/453* (2006.01)

(52) U.S. Cl. .................. 204/601; 204/604

(58) Field of Classification Search ........... 436/516; 204/601–605, 451–455
See application file for complete search history.

(56) References Cited

U.S. PATENT DOCUMENTS

| | | | |
|---|---|---|---|
| 4,816,123 A | 3/1989 | Ogan et al. | |
| 5,045,172 A | 9/1991 | Guzman | |
| 5,198,091 A | 3/1993 | Burolla et al. | |
| 5,202,010 A | 4/1993 | Guzman | |
| 5,246,577 A | 9/1993 | Fuchs et al. | |
| 5,318,680 A | 6/1994 | Fishman et al. | |
| 5,324,401 A | 6/1994 | Yeung et al. | |
| 5,340,452 A | 8/1994 | Brenner et al. | |
| 5,348,633 A | 9/1994 | Karger et al. | |
| 5,413,686 A | 5/1995 | Klein et al. | |
| 5,439,578 A | 8/1995 | Dovichi et al. | |
| 5,453,382 A | 9/1995 | Novotny et al. | |
| 5,498,324 A | 3/1996 | Yeung et al. | |
| 5,516,409 A | 5/1996 | Kambara | |
| 5,560,811 A | 10/1996 | Briggs et al. | |
| 5,582,705 A | 12/1996 | Yeung et al. | |
| 5,637,458 A | 6/1997 | Frankel et al. | |
| 5,730,850 A | 3/1998 | Kambara et al. | |
| 5,741,639 A | 4/1998 | Ensing et al. | |
| 5,800,692 A * | 9/1998 | Naylor et al. | 204/601 |
| 5,856,174 A | 1/1999 | Lipshutz et al. | |
| 5,944,971 A * | 8/1999 | Foote | 204/456 |
| 5,958,202 A | 9/1999 | Regnier et al. | |

(Continued)

FOREIGN PATENT DOCUMENTS

EP    0793098    9/1997

(Continued)

OTHER PUBLICATIONS

"Affinity Chromatography,"Cuatrecasas and Anfinsen, Annual Review of Biochemistry 40, pp. 259-278. No month available (1971).

(Continued)

*Primary Examiner*—Alex Noguerola
(74) *Attorney, Agent, or Firm*—Jeffer Mangels Butler & Marmaro, LLP

(57) ABSTRACT

An electrophoresis apparatus is generally disclosed for sequentially analyzing a single sample or multiple samples having one or more analytes in high or low concentrations. The apparatus comprises a relatively large-bore transport capillary which intersects with a plurality of small-bore separation capillaries. Analyte concentrators, having antibody-specific (or related affinity) chemistries, are stationed at the respective intersections of the transport capillary and separation capillaries to bind one or more analytes of interest. The apparatus allows the performance of two or more dimensions for the optimal separation of analytes.

42 Claims, 8 Drawing Sheets

U.S. PATENT DOCUMENTS

| | | | |
|---|---|---|---|
| RE36,350 E * | 10/1999 | Swedberg et al. ....... 210/198.2 | |
| 6,001,230 A | 12/1999 | Burolla | |
| 6,007,690 A | 12/1999 | Nelson et al. | |
| 6,010,607 A | 1/2000 | Ramsey | |
| 6,010,608 A | 1/2000 | Ramsey | |
| 6,013,165 A * | 1/2000 | Wiktorowicz et al. ...... 204/456 | |
| 6,020,208 A | 2/2000 | Hutchens et al. | |
| 6,150,180 A | 11/2000 | Parce et al. | |
| 6,224,728 B1 | 5/2001 | Oborny et al. | |
| 6,375,901 B1 | 4/2002 | Robotti et al. | |
| 6,387,234 B1 | 5/2002 | Yeung et al. | |
| 6,395,169 B1 | 5/2002 | Hindsgaul et al. | |
| 6,406,604 B1 * | 6/2002 | Guzman ...................... 204/601 | |
| 6,415,821 B1 | 7/2002 | Kamholz et al. | |
| 6,534,262 B1 | 3/2003 | McKernan et al. | |
| 6,544,396 B1 | 4/2003 | Cong et al. | |
| 6,554,986 B1 | 4/2003 | Mathies et al. | |
| 6,562,214 B1 | 5/2003 | Amrhein et al. | |
| 6,596,140 B1 | 7/2003 | Nordman et al. | |
| 6,613,212 B1 | 9/2003 | Siebert et al. | |
| 6,616,824 B1 | 9/2003 | Tanaka | |
| 6,627,453 B1 | 9/2003 | Hindsgaul et al. | |
| 6,635,164 B1 | 10/2003 | Anazawa et al. | |
| 6,875,403 B1 | 4/2005 | Liu et al. | |
| 2002/0054835 A1 | 5/2002 | Robotti et al. | |
| 2002/0058273 A1 | 5/2002 | Shipwash | |
| 2002/0115201 A1 | 8/2002 | Barenburg et al. | |
| 2003/0027354 A1 | 2/2003 | Geli | |
| 2003/0134415 A1 | 7/2003 | Yamanashi et al. | |

FOREIGN PATENT DOCUMENTS

| | | |
|---|---|---|
| EP | 1048950 | 11/2000 |
| EP | 1048951 | 11/2000 |
| EP | 0666980 B1 | 5/2002 |
| EP | 1357378 A2 | 10/2003 |
| WO | WO 95/10344 | 4/1995 |
| WO | WO 95/10344 A1 * | 4/1995 |
| WO | WO 97/11362 | 3/1997 |
| WO | WO 98/23950 | 6/1998 |
| WO | WO 00/30751 | 6/2000 |
| WO | WO 00/65354 | 11/2000 |
| WO | WO 02/44703 A2 | 6/2002 |
| WO | WO 02/48716 A2 | 6/2002 |
| WO | WO 02/059592 A2 | 8/2002 |
| WO | WO 03/27028 A1 | 4/2003 |
| WO | WO 03/038424 A1 | 5/2003 |
| WO | WO 03/48755 A1 | 6/2003 |
| WO | WO 03/059935 A2 | 7/2003 |
| WO | WO 03/087772 A2 | 10/2003 |

OTHER PUBLICATIONS

"Isotachophoresis Electrodesorption of Proteins from an Affinity Adsorbent on a Microscale," Kasicka and Prusik, Journal of Chromatography 273(1), pp. 117-128 (Mar. 11, 1983).

"Desorption Isotachophoresis—Quantitative Characterization of Sorption and Desorption Conditions," Kasicka and Prusik, Journal of Chromatography 273(1), pp. 75-80 (Feb. 22, 1985).

"The Use of a Concentration Step to Collect Urinary Components Separated by Capillary Electrophoresis and Further Characterization of Collected Analytes by Mass Spectrometry," Guzman et al., Journal of Liquid Chromatography 14(5), pp. 997-1015 (Mar. 1991).

"Enzymophoresis of Nucleic Acids by Tandem Capillary Enzyme Reactor-Capillary Zone Electrophoresis," Nashabeh and Ziad El Rassi, Journal of Chromatography 596(2), pp. 251-264 (Apr. 10, 1992).

"Switching Valve with Internal Micro Precolumn for On-Line Sample Enrichment in Capillary Zone Electrophoresis," Debets et al., Journal of Chromatography 608(1-2), pp. 151-158 (Sep. 11, 1992).

"On-Line Peptide Mapping by Capillary Electrophoresis," Amankwa and Kuhr, Analytical Chemistry 65(19), pp. 2693-2697 (Oct. 1, 1993).

"Preparation and Evaluation of an On-Line Preconcentrator for Capillary Electrophoresis," Hoyt, Jr. et al., Journal of Microcolumn Separations 5(4), pp. 325-330, No month available (1993).

"On-Line Sample Preconcentration on a Packet-Inlet Capillary for Improving the Sensitivity of Capillary Electrophoresis of Pharmaceuticals," Swartz and Merion, Journal of Chromatography 632(1-2), pp. 209-213 (Feb. 19, 1993).

"Immunoaffinity Capillary Electrophoresis Analysis of Cyclosporin in Tears," Phillips and Chmielinska, Biomedical Chromatography 8(5), pp. 242-246 (Sep.-Oct. 1994).

"Optimization of On-Line Peptide Mapping by Capillary Zone Electrophoresis," Licklider and Kuhr, Analytical Chemistry 66(24), pp. 4400-4407 (Dec. 15, 1994).

"The Use of Solid Phase Concentrators for On-Line Preconcentration of Metallothionein Prior to Isoform Separation by Capillary Zone Electrophoresis," Beattie et al., Electrophoresis 16(3), pp. 322-328 (Mar. 1995).

"Selective Preconcentration for Capillary Zone Electrophoresis Using Protein G Immunoaffinity Capillary Chromatography," Cole and Kennedy, Electrophoresis 16(4), pp. 549-556 (Apr. 1995).

"Sensitivity Enhancement and Second-Dimensional Information from Solid Phase Extraction-Capillary Electrophoresis of Entire High-Performance Liquid Chromatography Fractions," Strausbauch et al., Electrophoresis 16(4), pp. 541-548 (Apr. 1995).

"Michaelis-Menten analysis of immobilized enzyme by affinity capillary electrophoresis," Yoshimoto et al., Journal of Pharmaceutical and Biomedical Analysis 13(4-5), pp. 483-488 (Apr. 1995).

"Biomedical Applications of On-Line Preconcentration-Capillary Electrophoresis Using an Analyte Concentrator: Investigation of Design Options," Guzman, Journal of Liquid Chromatography 18(18&19), pp. 3751-3768 (Jun. 1995).

"Capillary enzymophoresis of nucleic acid fragments using coupled capillary electrophoresis and capillary enzyme microreactors having surface-immobilized RNA-modifying enzymes," Mechref and El Rassi, Electrophoresis 16(11), pp. 2164-2171 (Nov. 1995).

"Immobilization of Antibodies as a Versatile Tool In Hybridized Capillary Electrophoresis," Ensing and Paulus, Journal of Pharmaceutical and Biomedical Analysis 14(3), pp. 305-316 (Jan. 1996).

"On-Capillary Sample Preconcentration Incorporated in Chiral Capillary Electrophoresis," He et al., Analytical Sciences 12, pp. 177-181 (Apr. 1996).

"Preconcentration and Microreaction Technology On-Line with Capillary Electrophoresis," Tomlinson et al., Journal of Chromatography A 744(1-2), pp. 3-15 (Sep. 13, 1996).

"Protein Identification by Solid Phase Microextraction-Capillary Zone Electrophoresis-Microelectrospray-Tandem Mass Spectrometry," Figeys et al., Nature Biotechnology 14(11), pp. 1579-1583 (Nov. 1996).

"Consecutive protein digestion and peptide derivatization employing an on-line analyte concentrator to map proteins using capillary electrophoresis," Guzman, In: Capillary Electrophoresis in Analytical Biotechnology (Edited by Pier Giorgio Righetti), CRC Series in Analytical Biotechnology, Chapter 4, pp. 101-121, CRC Press, Inc. Boca Raton, Florida (1996, No month available).

"Identification of Proteins by Capillary Electrophoresis-Tandem Mass Spectrometry. Evaluation of an On-Line Solid-Phase Extraction Device," Figeys, et al., Journal of Chromatography A 763(1-2), pp. 295-306 (Feb. 28, 1997).

"High-Throughput DNA Sequencing on a Capillary Array Electrophoresis System," Marsh et al., Journal of Capillary Electrophoresis 4(2), pp. 83-89 (Mar.-Apr. 1997).

"New Approaches in Clinical Chemistry: On-Line Analyte Concentration and Microreaction Capillary Electrophoresis for the Determination of Drugs, Metabolic Intermediates, and Biopolymers in Biological Fluids," Guzman et al., Journal of Chromatography B 697(1-2), pp. 37-66 (Sep. 12, 1997).

"Automated Microanalysis Using Magnetic Beads with Commercial Capillary Electrophoresis Instrumentation," Rashkovetsky et al., Journal of Chromatography A, 781(1-2), pp. 197-204 (Sep. 26, 1997).

"A Novel m-ESI Source for Coupling Capillary Electrophoresis and Mass Spectrometry: Sequence Determination of Tumor Peptides at the Attomole Level," Settlage et al., Journal of Microcolumn Separation 10(3), pp. 281-285, No month available (1998).

"Analysis of Multiplexed Short-Tandem Repeat (STR) Systems Using Capillary Array Electrophoresis," Mansfield et al., Electrophoresis 19(1), pp. 101-107 (Jan. 1998).

"A New Design for Large, Dilute Sample Loading In Capillary Electrophoresis," Barroso and de Jong, Journal of Capillary Electrophoresis 5(1-2), pp. 1-7 (Jan.-Feb.-Mar.-Apr. 1998).

"Affinity Capillary Electrophoresis: A Physical-Organic Tool for Studying Interactions in Biomolecular Recognition," Cotton et al., Electrophoresis 19(3), pp. 367-382 (Mar. 1998).

"Survey of Recent Advances in Analytical Applications of Immunoaffinity Chromatography," Hage, Journal of Chromatography B 715(1), pp. 3-28 (Sep. 11, 1998).

"Affinity Capillary Electrophoresis: Important Application Areas and Some Recent Developments," Heegaard et al., Journal of Chromatography B 715(1), pp. 29-54 (Sep. 11, 1998).

"Recycling Immunoaffinity Chromatography for Multiple Analyte Analysis in Biological Samples," Phillips and Krum, Journal of Chromatography B 715(1), pp. 55-63 (Sep. 11, 1998).

"Nanoflow Solvent Gradient Delivery from a Microfabricated Device for Protein Identifications by Electrospray Ionization Mass Spectrometry," Figeys and Aebersold, Analytical Chemistry 70(18), pp. 3721-3727 (Sep. 15, 1998).

"Fabrication of Nanocolumns for Liquid Chromatography," He et al., Analytical Chemistry 70(18), pp. 3790-3797 (Sep. 15, 1998).

"Parallel Molecular Genetic Analysis," McKenzie et al., European Journal of Human Genetic 6(5), pp. 417-429 (Sep.-Oct. 1998).

"Optimization of Solid Phase Microextraction-Capillary Zone Electrophoresis-Mass Spectrometry for High Sensitivity Protein Identification," Figeys et al., Electrophoresis 19(13), pp. 2338-2347 (Oct. 1998).

"Analysis of Recombinant Cytokines in Human Body Fluids by Immunoaffinity Capillary Electrophoresis," Phillips and Dickens, Electrophoresis 19(16-17), pp. 2991-2998 (Nov. 1998).

"Evaluation of Adsorption Preconcentration/Capillary Zone Electrophoresis/Nanospray Mass Spectrometry for Peptide and Glycoprotein Analyses," Bateman et al., Journal of Mass Spectrometry 33(11), pp. 1109-1123 (Nov. 1998).

"Precolumn Affinity Capillary Electrophoresis for the Identification of Clinically Relevent Proteins in Human Serum: Application to human Cardiac Traponin I," Dalluge and Sander, Analytical Chemistry 70(24), pp. 5339-5343 (Dec. 15, 1998).

"On-Line Bioaffinity, Molecular Recognition, and Preconcentration in CE Technology," Guzman, LC-GC 17(1), pp. 16-27 (Jan. 1999).

"Capillary Array Electrophoresis DNA Sequencing," Kheterpal and Mathies, Analytical Chemistry 71(1), pp. 31A-37A (Jan. 1, 1999).

"Membrane Preconcentration CE," Yang et al., Analytical Chemistry 71(5), pp. 183A-189A (Mar. 1, 1999).

"An On-Line Preconcentrator and the Evaluation of Electrospray Interfaces for the Capillary Electrophoresis/Mass Spectrometry of Peptides," Herring and Qin, Rapid Communications in Mass Spectrometry 13(1), pp. 1-7, No month available (1999).

"SDS Capillary Electrophoresis of Proteins in Microfabricated Channels," Yao et al., Proceedings of the National Academy of Sciences USA 96(10), pp. 5372-5377 (May 11, 1999).

"Miniaturised on-line solid-phase extraction for enhancement of concentration sensitivity in capillary electrophoresis," Petersson et al., Journal of Chromatography A 841(2), pp. 249-261 (May 14, 1999).

"On-line solid-phase preconcentration for sensitivity enhancement in capillary electrophoresis," Bonneil and Waldron, Journal of Capillary Electrophoresis 6(3-4), pp. 61-73 (May-Aug. 1999).

"Monitoring the purity of a synthetic peptide by capillary electrophoresis: Utilization of an on-line preconcentration method for improved separation and detection sensitivity," Vizioll et al., Journal of Capillary Electrophoresis 6(3-4), pp. 109-118 (May-Aug. 1999).

"Simultaneous Genetic Typing from Multiple Short Tandem Repeat Loci Using a 96-Capillary Array Electrophoresis System," Gao et al., Electrophoresis 20(7), pp. 1518-1526 (Jun. 1999).

"Dynamic Hybridization on a Chip Using Paramagnetic Beads," Fan et al., Analytical Chemistry 71(21), pp. 4851-4859 (Nov. 1, 1999).

"Radial Capillary Array Electrophoresis Microplate and Scanner for High-Performance Nucleic Acid Analysis," Shi et al., Analytical Chemistry 71(23), pp. 5354-5361 (Dec. 1, 1999).

"Sheath less Preconcentration-Capillary Zone Electrophoresis-Mass Spectrometry Applied to Peptide Analysis," Begona Barroso and de Jong, Journal of the American Society for Mass Spectrometry 10(12), pp. 1271-1278 (Dec. 1999).

"Characterization of a solid-phase extraction device for discontinuos on-line preconcentration in capillary electrophoresis-based peptide mapping," Bonneil and Waldron, Journal of Chromatography B 736(1-2), pp. 273-287 (Dec. 24, 1999).

"Strategies to improve the sensitivity in capillary electrophoresis for the analysis of drugs in biolical fluids," Hempel, Electrophoresis 21(4), pp. 691-698 (Mar. 2000).

"Mapping the phosphorylation sites of proteins using on-line immobilized metal affinity chromatography/capillary electrophoresis/electrospray ionization multiple stage tandem mass spectrometry," Cao and Stults, Rapid Communication Mass Spectrometry 14(17), pp. 1600-16006, No month available (2000).

"Packing columns for capillary electrochromatography," Colon et al., Journal of Chromatography A 887(1-2), pp. 43-53 (Jul. 28, 2000).

"Stationary phases for capillary electrochromatography," Pursch and Sander, Journal of Chromatography A 887(1-2), pp. 313-326 (Jul. 28, 2000).

"On-line preconcentration methods for capillary electrophoresis," Osbourn et al., Electrophoresis 21(14), pp. 2768-2779 (Aug. 2000).

"Alternative methods providing enhanced sensitivity and selectivity in capillary electrophoresis," Schweltz et al., Journal of Chromatography A 892(1-2), pp. 203-217 (Sep. 15, 2000).

"Electrochromatography," Smith and Carter-Finch, Journal of Chromatography A 892(1-2), pp. 219-255 (Sep. 15, 2000).

"Advances in column technology and instrumentation in capillary electrochromatography," Pyell, Journal of Chromatography A 892(1-2), pp. 257-278 (Sep. 15, 2000).

"Sample preconcentration by field amplification stacking for microchip-based capillary electrophoresis," Lichtenberg et al., Electrophoresis 22(2), pp. 258-271 (Jan. 2001).

"Analysis of single-cell cultures by immunoaffinity capillary electrophoresis with laser-induced fluorescence detection," Phillips, Luminescence 16(2), pp. 145-152 (Mar.-Apr. 2001).

"Sol-gel technique for the preparation of beta-cyclodextrin derivative stationary phase in open-tubular capillary electrochromatography," Wang et al., Electrophoresis 22(11), pp. 2167-2172 (Jul. 18, 2001).

"On-line sample preconcentration in capillary electrophoresis, focused on the determination of proteins and peptides," Strolnk et al., Electrophoresis 22(12), pp. 2374-2383 (Aug. 2001).

"Approaches to enhancing the sensitivity of capillary electrophoresis methods for the determination of inorganic and small organic anions," Breadmore and Haddad, Electrophoresis 22(12), pp. 2464-2489 (Aug. 2001).

"Robust and cost-effective capillary electrophoresis-mass spectrometry interfaces suitable for combination with on-line analyte preconcentration," Waterval et al., Electrophoresis 22(13), pp. 2701-2708 (Aug. 2001).

"Capillary electrophoretic bioanalysis of therapeutically active peptides with UV and mass spectrometric detection after on-capillary preconcentration," Waterval et al., Electrophoresis 22(13), pp. 2709-2718 (Aug. 2001).

"The use of selective adsorbents in capillary electrophoresis-mass spectrometry for analyte preconcentration and microreactions: A powerful three-dimensional tool for multiple chemical and biological applications," Guzman and Stubbs, Electrophoresis 22(17), pp. 3602-3628 (Oct. 2001).

"Sample preparation with fiber-in-tube solid-phase microextraction for capillary electrophoretic separation of tricyclic antidepressant drugs in human urine," Jinno et al., Electrophoresis 22(17), pp. 3785-3790 (Oct. 2001).

"Exploiting lectin affinity chromatography in clinical diagnosis," Satish and Surolia, Journal of Biochemical and Biophysics Methods 49(1-3), pp. 625-640 (Oct. 30, 2001).

"On-line preconcentration in capillary electrochromatography using a porous monolith together with solvent gradient and sample stacking," Quirino et al., Analytical Chemistry 73(22), pp. 5557-5563 (Nov. 15, 2001).

"Sensitivity enhancement by on-line preconcentration and in-capillary derivatization for the electrophoretic determination of amino acids," Latorre et al., Electrophoresis 22(20), pp. 4355-4361 (Dec. 2001).

"Improved method for pepsinolysis of mouse IgG(1) molecules to F(ab')2 fragments," Wilson et al., Journal of Immunological Methods 260(1-2), pp. 29-36 (Feb. 1, 2002).

"Application of microfluidic devices to proteomics research: Identification of trace level protein digests and affinity capture of target peptides," Li et al., Molecular & Cellular Proteomics 1(2), pp. 157-168 (Feb. 2002).

"Toward a microchip-based solid-phase extraction method for isolation of nucleic acids," Wolfe et al., Electrophoresis 23(5): 727-733 (Mar. 2002).

"Immunoaffinity screening with capillary electrophochromatography," Mayer et al., Electrophoresis 23(9), pp. 1255-1262 (May 2002).

"On-column ion-exchange preconcentration of inorganic anions in open tubular capillary chromatography with elution using transient-isotachophoretic gradients. 3. Implementation and method development," Breadmore et al., Analytical Chemistry 74(9), 2112-2118 (May 1, 2002).

"On-line trypsin-encapsulated enzyme reactor by the sol-gel method integrated into capillary electrophoresis," Sakai-Kato et al., Analytical Chemistry 74(13):2943-2949 (Jul. 1, 2002).

"Sweeping: Concentration mechanism and applications to high-sensitivity analysis in capillary electrophoresis," Quirino et al., Journal of Chromatography A 965(1-2), pp. 357-3773 (Aug. 2002).

"On-chip chromatography: the last twenty years," de Mello, Lab on a Chip 2(3), pp. 48N-54N (Aug. 2002).

"A new type of capillary column for open-tubular electrochromatography," Zhao et al., Electrophoresis 23(17), pp. 2990-2995 (Sep. 2002).

"On-line drug metabolism system using microsomes encapsulated in a capillary by sol-gel method and integrated into capillary electrophoresis," Sakai-Kato et al., Analytical Biochemistry 308(2), pp. 278-284 (Sep. 15, 2002).

"An integrated solid-phase extraction system for sub-picomolar detection," Jemere et al., Electrophoresis 23(20), pp. 3537-3544 (Oct. 2002).

"Integration of solid-phase extraction membranes for sample multiplexing: application to rapid protein identification from gel-isolated protein extracts," Bonnell et al., Electrophoresis 23(20), pp. 3589-3598 (Oct. 2002).

"Advances in sol-gel based columns for capillary electrochromatography: sol-gel open-tubular columns," Malik, Electrophoresis 23(22-23), pp. 3973-3992 (Nov. 2002).

"On-chip coupling of isoelectric focusing and free solution electrophoresis for multidimensional separations," Herr et al., Analytical Chemistry 75(5), pp. 1180-1187 (Mar. 1, 2003).

"Analysis of intracellular regulatory proteins by immunoaffinity capillary electrophoresis coupled with laser-induced fluorescence detection," Phillips and Smith, Biomedical Chromatography 17(2-3), pp. 182-187 (Mar. 2003).

"Immuno-based sample preparation for trace analysis," Hennion and Pichon, Journal of Chromatography A 1000(1-2), pp. 29-52 (Jun. 6, 2003).

"Silica gel-based monoliths prepared by the sol-gel method: facts and figures," Siouffi, Journal of Chromatography A 1000(1-2), pp. 801-818 (Jun. 6, 2003).

"On-line preconcentration strategies for trace analysis of metabolites by capillary electrophoresis," Britz-McKibbin and Terabe, Journal of Chromatography A 1000(1-2), pp. 917-934 (Jun. 6, 2003).

"Small structures fabricated using ash-forming biological materials as templates," Kim, Biomacromolecules 4(4), pp. 908-913 (Jul.-Aug. 2003).

"On-line preconcentration in capillary electrophoresis using monolithic methacrylate porous," Baryla and Toltl, Analyst 128(8), pp. 1009-1012 (Aug. 2003).

"Capillary electrochromatography and preconcentration of neutral compounds on poly(dimethylsiloxane) microchips," Ro et al., Electrophoresis 24(18), pp. 3253-3259 (Sep. 2003).

"Preparation of hollow silica microspheres in W/O emulsions with polymers," Park et al., Journal of Colloid and Interface Science 266(1), pp. 107-114 (Oct. 1, 2003).

"Fluidic preconcentrator device for capillary electrophoresis of proteins," Astorga-Wells and Swerdlow, Analytical Chemistry 75(19), pp. 5207-5212 (Oct. 1, 2003).

"A microfluidic electrocapture device in sample preparation for protein analysis by MALDI spectrometry," Astorga-Wells et al., Analytical Chemistry 75(19), pp. 5213-5219 (Oct. 1, 2003).

"The 'right' size in nanobiotechnology," Whitesides, Nature Biotechnology 21(10), pp. 1161-1163 (Oct. 2003).

"Fabrication of novel biomaterials through molecular self-assembly," Zhang, Nature Biotechnology 21(10), pp. 1171-1178 (Oct. 2003).

"Integrated nanoliter systems," Hong and Quake, Nature Biotechnology 21(10), pp. 1179-1183 (Oct. 2003).

"Small-scale systems for in vivo drug delivery," La Van et al., Nature Biotechnology 21(10), pp. 1184-1191 (Oct. 2003).

"Electrochemical DNA detectors," Drummond et al., 21(10), Nature Biotechnology 21(10), 1192-1199 (Oct. 2003).

"Low-attomole electorspray ionization MS and MS/MS analysis of protein tryptic digests using 20-µm-i.d. polystyrene-divinylbenzene monolithic capillary columns," Ivanov et al., Analytical Chemistry 75(20), pp. 5306-5316.

"Dual-function microanalytical device by in situ photolithographic grafting of porous polymer monolith: integrating solid-phase extraction and enzymatic digestion for peptide mass mapping," Peterson et al., Analytical Chemistry 75(20), pp. 5328-5335 (Oct. 15, 2003).

"Phosphoprotein isotope-coded solid-phase tag approach for enrichment and quantitative analysis of phosphopeptides from complex mixtures," Qian et al., Analytical Chemistry 75(20), pp. 5441-5450 (Oct. 15, 2003).

"Development of a poly(dimethylsiloxane) interface for on-line capillary column liquid chromatography-capillary electrophoresis coupled to sheathless electrospray ionization time-of-flight mass spectrometry," Bergstrom et al., Analytical Chemistry 75(20), pp. 5461-5467 (Oct. 15, 2003).

"Chip-based solid-phase extraction pretreatment for direct electrospray mass spectrometry analysis using an array of monolithic columns in a polymeric substrate," Tan et al., Analytical Chemistry 75(20), pp. 5504-5511 (Oct. 15, 2003).

"Biochemical analisis with microfluidic systems," Bilitewski et al., Analytical and Bioanalytical Chemistry 377(3), pp. 556-569 (Oct. 2003).

"The puzzle of the proteome," Willis, Modern Drug Discovery 6(10), pp. 26-30 (Oct. 2003).

* cited by examiner

MULTI-DIMENSIONAL ELECTROPHORESIS APPARATUS

This application is a continuation of U.S. application Ser. No. 09/436,186, filed Nov. 8, 1999, now U.S. Pat. No. 6,406,604.

FIELD OF THE INVENTION

The present invention relates generally to the analysis of chemical and biological materials and, more particularly, to an improved electrophoresis apparatus which simultaneously performs multiple analyses on a plurality of analytes.

BACKGROUND OF THE INVENTION

Electrophoresis is a known technique for separating and characterizing constituent chemical and/or biological molecules, or analytes, present in simple and complex matrices undergoing analysis. Candidate sample compounds include drugs, proteins, nucleic acids, peptides, metabolites, biopolymers and other substances which exist in simple and complex forms.

Conventional systems are based on interchangeable cartridges which house a thin capillary tube equipped with an optical viewing window that cooperates with a detector. Sample solutions and other necessary fluids are placed in vials (cups) positioned beneath inlet and outlet ends of the capillary tube by means of a rotatable table.

When high voltage is applied to a capillary filled with an appropriate solution and/or matrix, molecular components migrate through the tube at different rates and physically separate. The direction of migration is biased toward an electrode with a charge opposite to that of the molecules under investigation. As the molecules pass the viewing window, they are monitored by a UV or other detector which transmits an absorbance or appropriate signal to a recorder. The absorbance or appropriate values are plotted as peaks which supply analytical information in the form of electropherograms.

Electrophoresis separation relies on the different migration of charged particles in an electric field. Migration speed is primarily influenced by the charge on a particle which, in turn, is determined by the pH of the buffer medium. Electric field strength and molecular size and shape of the analyte also influence migration behavior.

Electrophoresis is a family of related techniques that perform high efficiency separations of large and small molecules. As one embodiment of this science, capillary electrophoresis is effective for obtaining rapid and high separations in excess of one-hundred-thousand plates/meter. Because it is a non-destructive technique, capillary electrophoresis preserves scarce physical samples and reduces consumption of reagents. A fused silica (quartz) capillary, with an inner bore diameter ranging from about 5 microns to about 200 microns and a length ranging from about 10 centimeters to about 100 centimeters, is filled with an electrically conductive fluid, or background electrolyte, which is most often a buffer. Since the column volume is only about 0.5 to about 30 microliters, the sample introduction volume is usually measured in nanoliters, picoliters and femtoliters (ideally 2% of the total volume of the column). As a consequence, the mass sensitivity of the technique is quite high.

Improved instrumentation and buffer-specific chemistries now yield accurate peak migrations and precise area counts for separated analytes. But, capillary electrophoresis is still limited by concentration sensitivity.

To overcome this deficiency, a series of solid-phase micro-extraction devices have been developed for selective and non-selective molecular consolidation. These devices, which are used on-line with a capillary tube, are commonly known as analyte concentrators containing affinity probes to bind target compounds. Typical embodiments are described in U.S. Pat. No. 5,202,010 which is incorporated by reference in this disclosure. Other relevant teachings are provided by U.S. Pat. No. 5,741,639 which discloses the use of molecular recognition elements; and U.S. Pat. No. 5,800,692 which discloses the use of a pre-separation membrane for concentrating a sample.

Even with the advent of analyte concentrators, there is still a need to improve the sensitivity levels for samples that exist in sub-nanomolar quantities. This deficit is particularly acute in the clinical environment where early detection of a single molecule may be essential for the identification of a life-threatening disease.

Known capillary electrophoresis instruments are also limited by low-throughput, i.e., the number of samples that can be analyzed in a specified period of time. U.S. Pat. No. 5,045,172, which is incorporated by reference, describes an automated, capillary-based system with increased analytical speed. The '172 patent represents a significant improvement over the prior art. But, throughput is still relatively low because the instrument uses only one capillary which performs single sample analyses in approximately 30 minutes.

U.S. Pat. No. 5,413,686 recognizes the need for a multi-functional analyzer using an array of capillary tubes. Like other disclosures of similar import, the '686 patent focuses on samples having relatively high concentrations. There is no appreciation of the loadability and sensitivity necessary for analyzing diluted samples, or samples present at low concentrations in a variety of liquids or fluids.

Based on these deficiencies, there exists an art-recognized need for an electrophoresis instrument having higher loadability, better detectability of constituent analytes, faster throughput and multi-functional capability for analyzing a plurality of components in a single sample and/or a plurality of samples with high and low concentrations using a variety of chromophores, detectors and/or pre-concentration devices.

OBJECTS OF THE INVENTION

Accordingly, it is a general object of the present invention to provide an improved electrophoresis apparatus having at least one transport capillary, at least one separation capillary and an analyte concentrator positioned therebetween;

It is another object of the present invention to provide an electrophoresis apparatus having greater operating efficiency, detectability and throughput.

An additional object of the present invention is to provide a user-friendly, sample preparation step which is designed to eliminate unwanted analytes that occupy binding sites and contaminate the inner walls of capillaries or channels.

A further object of the present invention is to provide an electrophoresis apparatus that can analyze multiple samples having a single constituent, or multiple constituents of a single sample.

It is a further object of the present invention to provide an electrophoresis apparatus which uses more than one analyte concentrator to sequentially bind more than one analyte in a single complex matrix, or in multiple matrices of simple or complex configuration.

It is yet another object of the present invention to provide an electrophoresis apparatus having enhanced loadability and sensitivity which is capable of analyzing samples present in a wide range of concentrations, including those found at low concentrations in diluted liquids or fluids with simple or complex matrices.

It is a further object of the present invention to provide an electrophoresis apparatus that delivers high-throughput for screening and analyzing a wide variety of samples in multiple application areas, utilizing a single or multiple dimension separation principle or mode.

Another object of the present invention is to provide an electrophoresis apparatus which uses more than one separation method to sequentially permit binding to, and elution from, an analyte concentrator to effect the separation of one or more analytes.

It is another object of the present invention to provide an automated, miniaturized desk-top electrophoresis apparatus for bioanalysis and other applications.

Additional objects of the present invention will be apparent to those skilled in the relevant art.

SUMMARY OF THE INVENTION

In one aspect of the invention, a sample including a number of analytes of interest is passed through a relatively large-bore transport capillary orthogonal to a plurality of smaller-bore separation capillaries. An analyte concentrator is positioned at each intersection of the transport capillary and separation capillaries.

After the sample has been passed through each of the analyte concentrators, and after the analytes of importance are captured by each concentrator matrix, a selected buffer is applied to each analyte concentrator to free the system of salts and other non-relevant components. For example, a typical buffered solution is sodium tetraborate having a pH in the range of 7.0 to 9.0. The bound analytes are then eluted from each concentrator matrix in a sequentially time-controlled fashion using an aliquot or plug of an optimal eluting solution. The process continues until each of the analytes has been removed from the concentrator matrices and passed through the detector by high resolution electrophoresis migration. To increase the sensitivity of the analytes, an additional analyte concentrator containing a chromophoric reagent may be placed in one or more of the separation capillaries to react with the analyte present in that capillary. Alternatively, the eluting solution may contain a chromophoric reagent allowing decoupling and derivatization to occur simultaneously. The derivatized analytes can then be isolated in the separation capillary.

To separate and analyze multiple samples with the electrophoresis apparatus of the invention, individual separation capillaries are provided, each of which contains an analyte concentrator that enriches the analytes present in diluted solutions of low concentration. Multiple elutions are carried out in a manner similar to that performed when analyzing a single sample. Effective results can also be achieved using solutions that contain an appropriate eluting chemical and a chromophoric reagent to simultaneously elute the targeted analyte and enhance sensitivity. As with a single-sample analyzer, an extra analyte concentrator may be placed in one or more of the separation capillaries to allow on-line derivatization of analytes to achieve even further enhancement of concentration sensitivity. In addition, an extra analyte concentrator may be placed in one or more of the separation capillaries to permit biochemical reactions, such as the on-line cleavage of proteins to generate peptides.

An analyte concentrator may also be used to quantify enzymatic products generated by the action of one or more pharmacological agents during a specific enzyme reaction. Furthermore, the use of an analyte concentrator coupled to a different mode of electrophoresis can be used to differentiate structurally related substances present in biological fluids or tissue specimens. For example, the identification and characterization of natural proteins from artificially-made proteins or other chemicals in serum.

All reactions described above can be performed in an apparatus containing a format that includes either capillaries or channels. In addition, the migration of analytes can be accomplished by an electrical or mechanical pump.

DETAILED DESCRIPTION OF THE INVENTION

Figure 1:
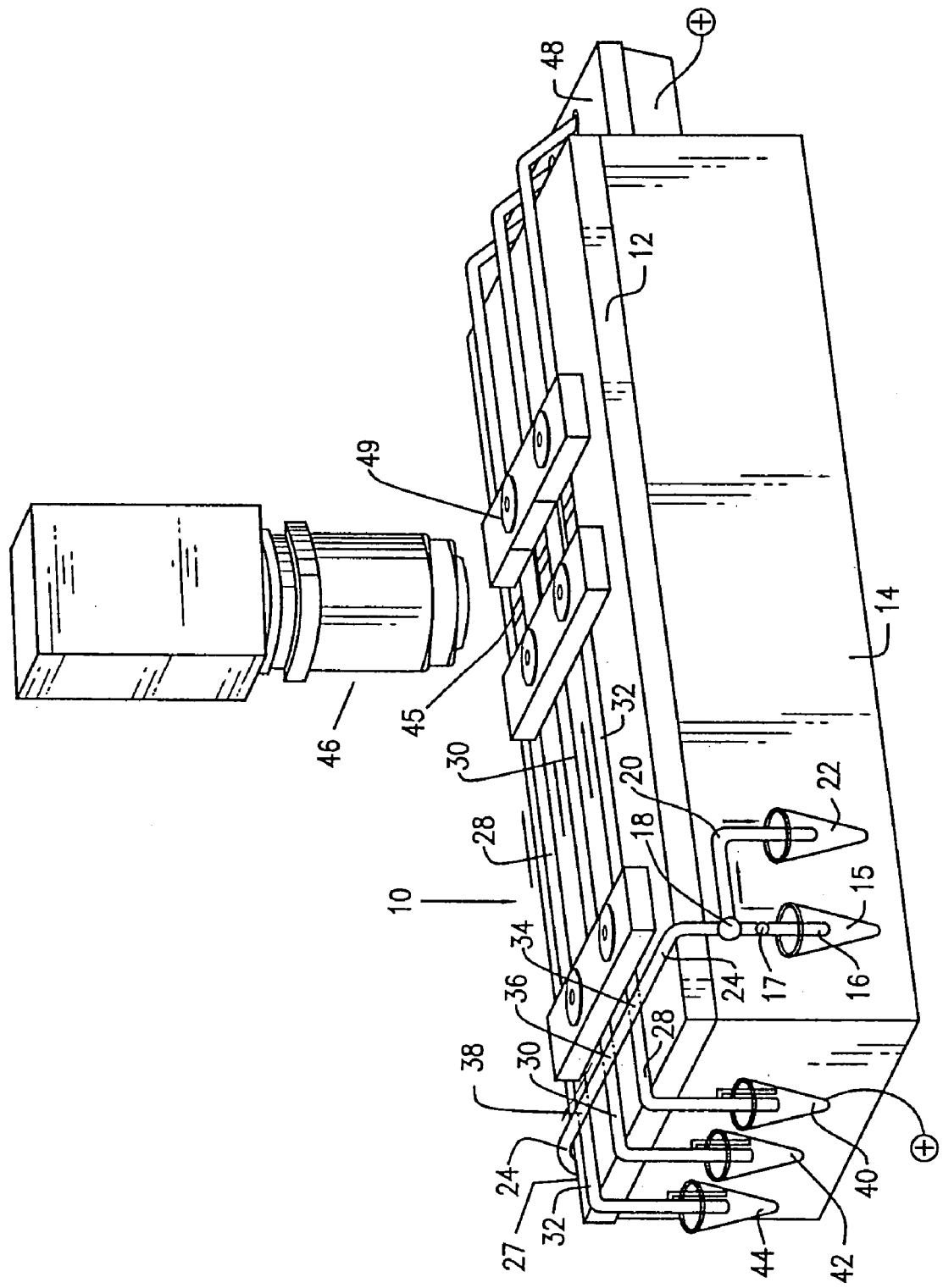
FIG. 1 is a perspective view of the electrophoresis apparatus of the present invention.

FIG. 1 illustrates electrophoresis apparatus 10 of the present invention. In its elementary mode (e.g., FIG. 8), apparatus 10 performs single sample studies on chemical or biological matrices having constituents or analytes of interest. But, according to the operating principles shown and described, apparatus 10 can perform multiple analyses by detecting and measuring the presence of a plurality of analytes (for example, three). Suitable and representative analytes may include narcotics, glucose, cholesterol or pharmaceutical drugs that may be present in urine or whole blood, as well as small and large molecular weight substances having simple and complex structures.

As shown in FIG. 1, apparatus 10 includes platform 12 having side wall 14. Sample cup 15 is mounted laterally on side wall 14. A large-bore (150–300 mm in length× 500–2000 µm I.D.), non-selective introduction capillary 16 and large-volume (1–3 ml) analyte concentrator 17 connect sample cup 15 to a first input of valve 18 which is coupled, by capillary 20, to waste container 22 positioned on side wall 14 adjacent to sample cup 15. In a typical configuration, analyte concentrator 17 comprises a matrix-like assembly of the type shown in U.S. Pat. No. 5,202,010. The collective mass of the matrix is provided by large quantities of microstructures such as beads, platelets, chips, fibers, filament or the like. Individual substrates can be made from glass, plastic, ceramic or metallic compositions; and mixtures thereof. Coated or otherwise deposited onto the microstructures are immobilized analyte-specific antibodies or other affinity chemistries which are suitable for characterizing and separating particular analytes of interest. Representative antibodies include those which act against peptide hormones such as insulin, human growth hormone and erythropoietin. These antibodies are readily available from commercial vendors such as Sigma-Aldrich Co., St. Louis, Mo. and Peninsula Laboratories, Belmont, Calif.

The present invention contemplates a user-friendly, sample preparation step which is designed to eliminate unwanted analytes that occupy binding sites and contaminate the inner walls of capillaries or channels. This procedure will now be described with specific reference to apparatus 10 of FIG. 2.

A first output of valve 18 is placed in the closed position and a quantity of solution from sample cup 15 is introduced into analyte concentrator 17. Depending on its pre-selected matrix, analyte concentrator 17 traps, in a non-specific manner, many (up to 100 or more) different analytes, including the analytes under investigation. Sample cup 15 is then replaced by a buffer container (not shown). This replacement step may be accomplished by a rotatable table mechanism of the type described in U.S. Pat. No. 5,045,172. Thereafter, a quantity of buffer is injected through analyte concentrator 17 to remove excess amounts of sample and unwanted sample components. Because valve 18 remains closed during this operation, excess and unwanted samples are passed into waste container 22.

Figure 2:
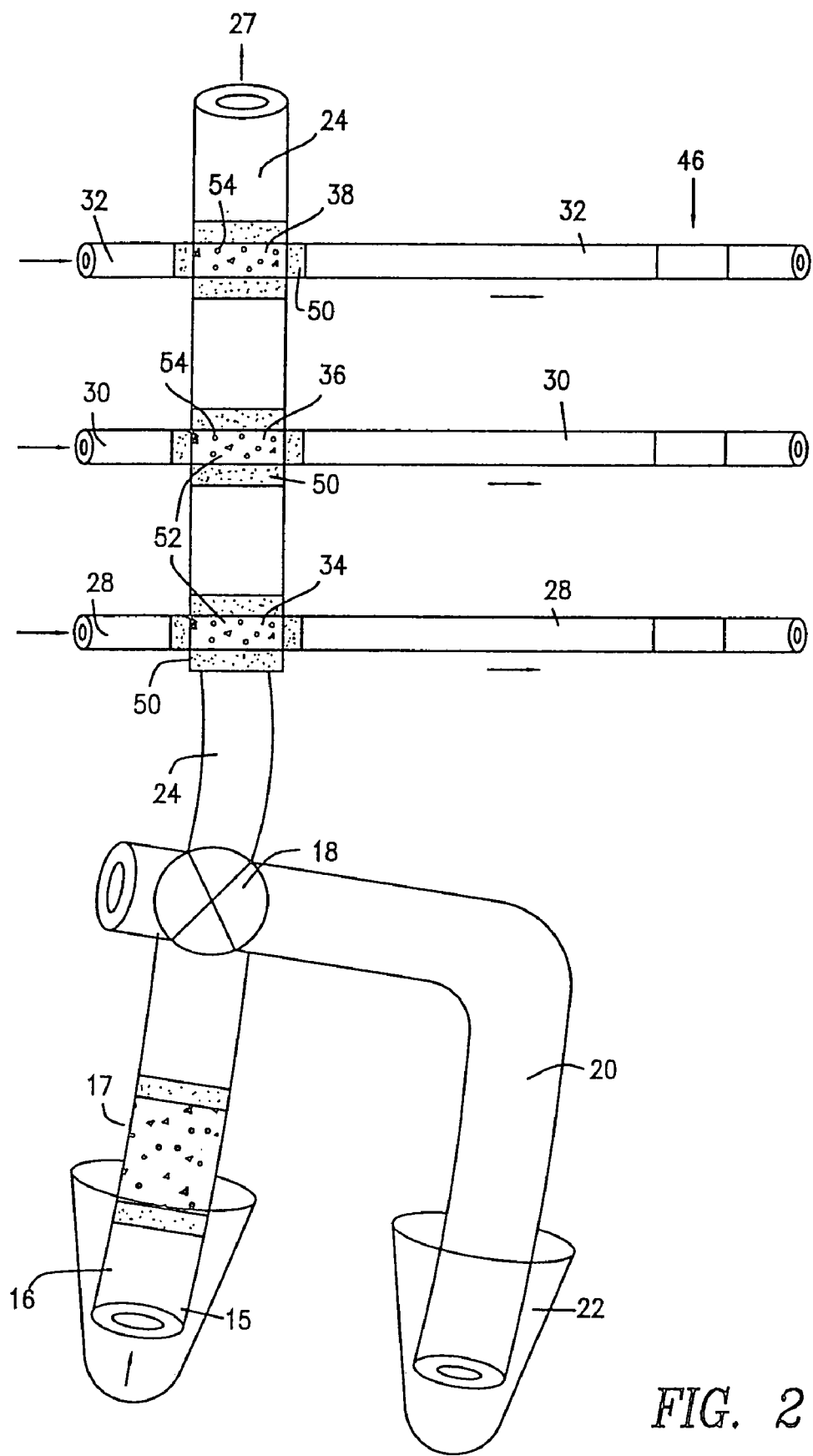
FIG. 2 is an enlarged, elevated view of a plurality of analyte concentrators stationed at the respective intersections of a large bore transport capillary and an equal plurality of small bore separation capillaries.

The remainder of apparatus 10 can now be considered. A second output of valve 18 communicates with transport capillary 24 which, as shown by FIG. 2, intersects a plurality, here shown as three, of narrow-bore (20–75 µm) separation capillaries 28, 30 and 32. Analyte concentrators 34, 36 and 38 are sequentially stationed at the intersections of transport capillary 24 and separation capillaries 28, 30 and 32 to trap or bind different analytes of interest.

Figure 3:
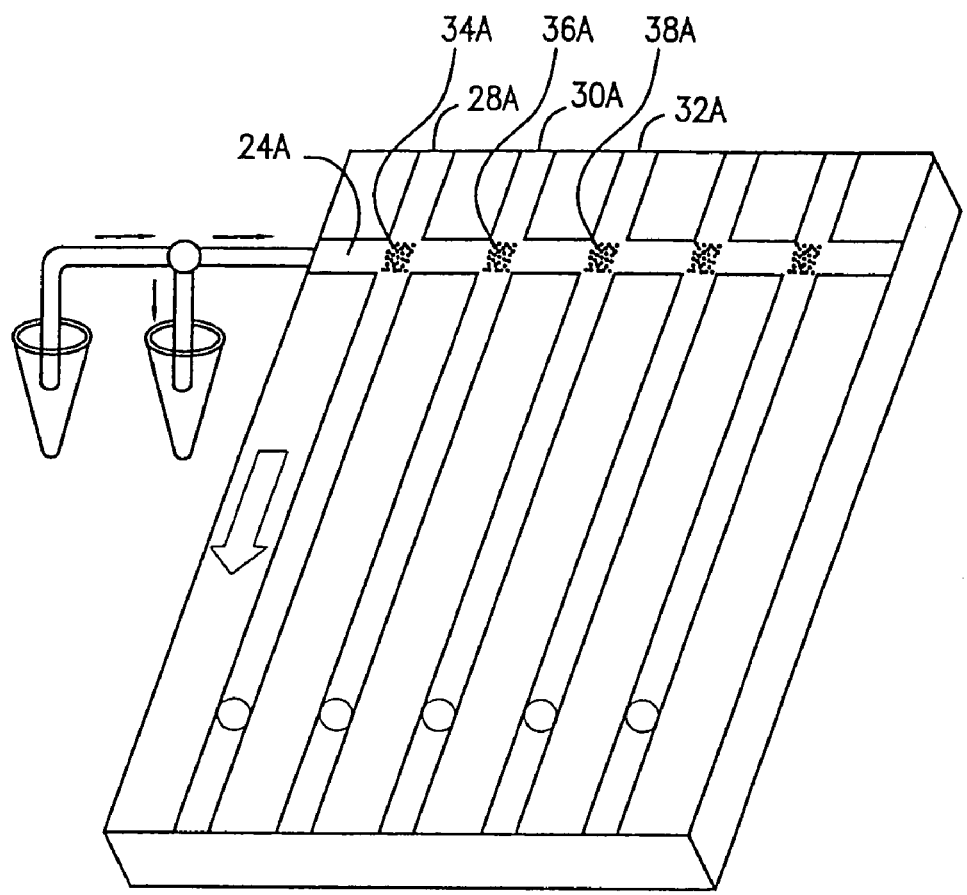
FIG. 3 is an elevated view of a second embodiment of the present invention, showing a plurality of analyte concentrators stationed at the respective intersections of an alternative transport channel and an equal plurality of separation channels.
Figure 3A:
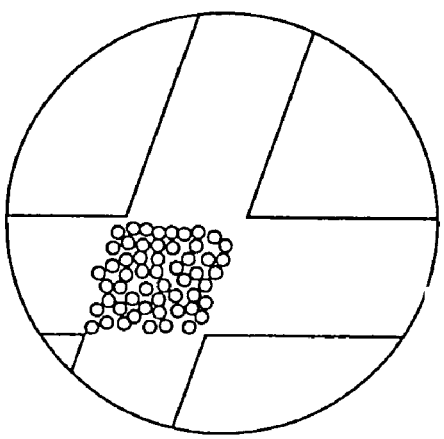
FIG. 3A is an enlarged view of the described intersection containing the analyte concentrator microstructure.

A first end (the left as viewed in FIG. 1) of separation capillary 28 is initially placed in buffer solution cup 40. In like manner, a first end of separation capillary 30 is placed in buffer solution cup 42; and a first end of separation capillary 32 is placed in buffer solution cup 44. A major portion of separation capillaries 28, 30 and 32 extend in parallel over the upper surface of platform 12 through detection zone 45 where the analytes respectively present in each of the separation capillaries are identified by an otherwise conventional detector 46. Separation capillaries 28, 30 and 32, which terminate at ground connection 48, may be secured to the upper surface of platform 12 by holders 49. Platform 12 can also take the form of an interchangeable cartridge with pre-positioned capillaries and analyte concentrators properly secured and aligned with respect to the optical system. In yet another embodiment, best shown in FIG. 3, transport channel 24A and separation channels 28A, 30A and 32A, having uniform and concave shapes, can be engraved, etched or otherwise formed into a glass or plastic microchip using known lithography or other manufacturing techniques. Analyte concentrators 34A, 36A and 38A are disposed at the respective intersections of transport channel 24A and separation channels 28A, 30A and 32A as previously described.

When the sample preparation step is complete, valve 18 is opened to the main system and a buffer (e.g., sodium tetraborate) is passed through introduction capillary 16 and analyte concentrator 17. At this time, the analytes of interest are released from analyte concentrator 17 using an eluting solution, along with other analyte constituents present in the sample. The analytes of interest and all the other analytes captured and released by concentrator 17 are passed through transport capillary 24 to analyte concentrators 34, 36 and 38 which, as described below with reference to FIG. 3, contain a large quantity of microstructures that are capable of binding different analytes of interest; that is, each of the analyte concentrators 34, 36 and 38 select and isolate a different one of the analytes under investigation. Excess amounts of sample then pass through the other end of transport capillary 24 to waste container 27. Transport capillary 24 is subsequently washed with running buffer until unwanted substances are removed.

Separation capillaries 28, 30 and 32 are filled hydrodynamically (pressure or vacuum) with an appropriate electrophoresis separation buffer which occupies the entire volume of the capillary or channel. Immobilized analytes on a solid support are stable for long periods of time. As a result, large numbers of analytes can be sequentially separated over time, thereby providing high throughput for the apparatus of the present invention. Separation capillary 28 is first activated by introducing a plug of an appropriate eluting buffer from cup 40 by hydrodynamic (pressure or vacuum) or electrokinetic methods to desorb or elute analytes bound to analyte concentrator 34. The eluting buffer is immediately followed by a freshly prepared electrophoresis separation buffer present in replacement cup 40. Then, the power supply connected to cup 40 is activated to begin the process of analyte separation.

As shown in Table 1, with insulin taken as representative, a typical analysis involves the targeted analyte of interest, its corresponding antibody, an appropriate buffer and eluting solution.

TABLE 1

| Antigen | Antibody | Sep. Buffer+ | Eluting Solution* |
|---------|----------|--------------|-------------------|
| Insulin | Anti-insulin antibody | Sodium tetraborate (pH 8.5) | Magnesium Chloride or Ethylene Glycol |

+Concentrations of electrophoresis separation buffer may range from 50 mM to 200 mM.
*Elution of other antigens or haptens may require a different eluting method. Effective eluting buffers include a 2 M solution of Magnesium Chloride and a 25% solution of Ethylene Glycol.

When the initial separation is complete, the next cycle, using separation capillary 30 and analyte concentrator 36, is performed in a similar manner, i.e., the analyte is eluted from concentrator 36 and then separated by eletrophoresis migration in separation capillary 30. During these operations, the power supply is connected to one analyte concentrator-separation capillary system at a time.

Separated analytes are then passed sequentially to detection zone 45 where each analyte is recognized and measured by detector 46 using, for example, known UV or fluorescence techniques. In one embodiment of the present invention, a single, bi-directional detector is indexed laterally above platform 12 to detect analytes of interest in separation capillaries 28, 30 and 32 or separation channels 28A, 30A and 32A. Other sub-assemblies could include a single, fixed detector and movable platform 12 which operates to position separation capillaries 28, 30 and 32 or separation channels 28A, 30A and 32A beneath the detector. Multiple detectors and movable platforms configured for X, Y and Z indexing are also contemplated.

Figure 4:
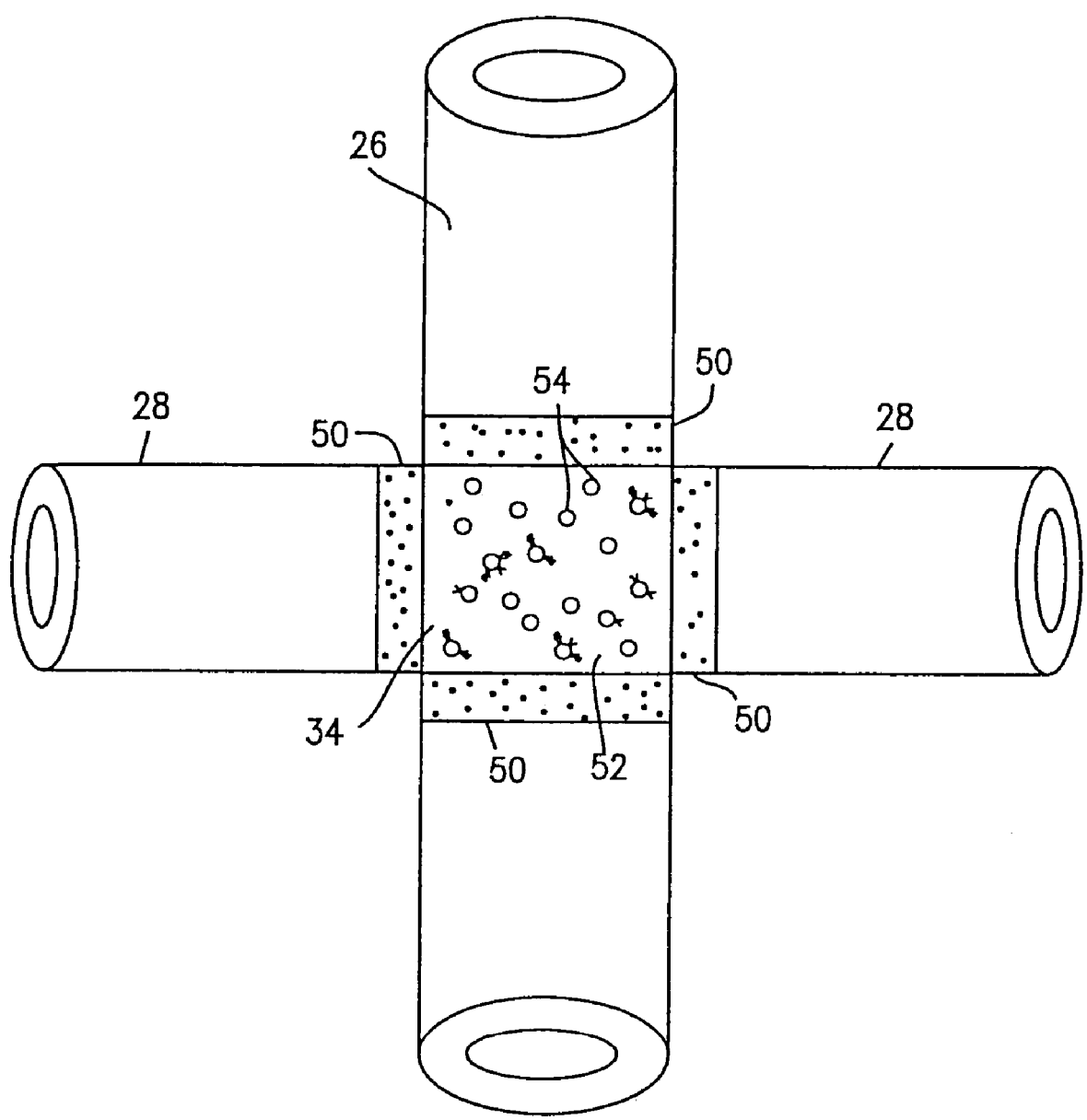
FIG. 4 is an enlarged, elevated view of an analyte concentrator stationed at the intersection of a transport capillary and a separation capillary.

FIG. 4 illustrates the location of analyte concentrator 34 stationed at the intersection of transport capillary 24 and separation capillary 28. As shown in FIG. 4, and in U.S. Pat. No. 5,203,010, porous end plates or frits 50, which permit fluid flow, are provided in transport capillary 24 and separation capillary 28 to act as barriers for holding microstructures 54 in analyte concentrator 34.

Figure 5:
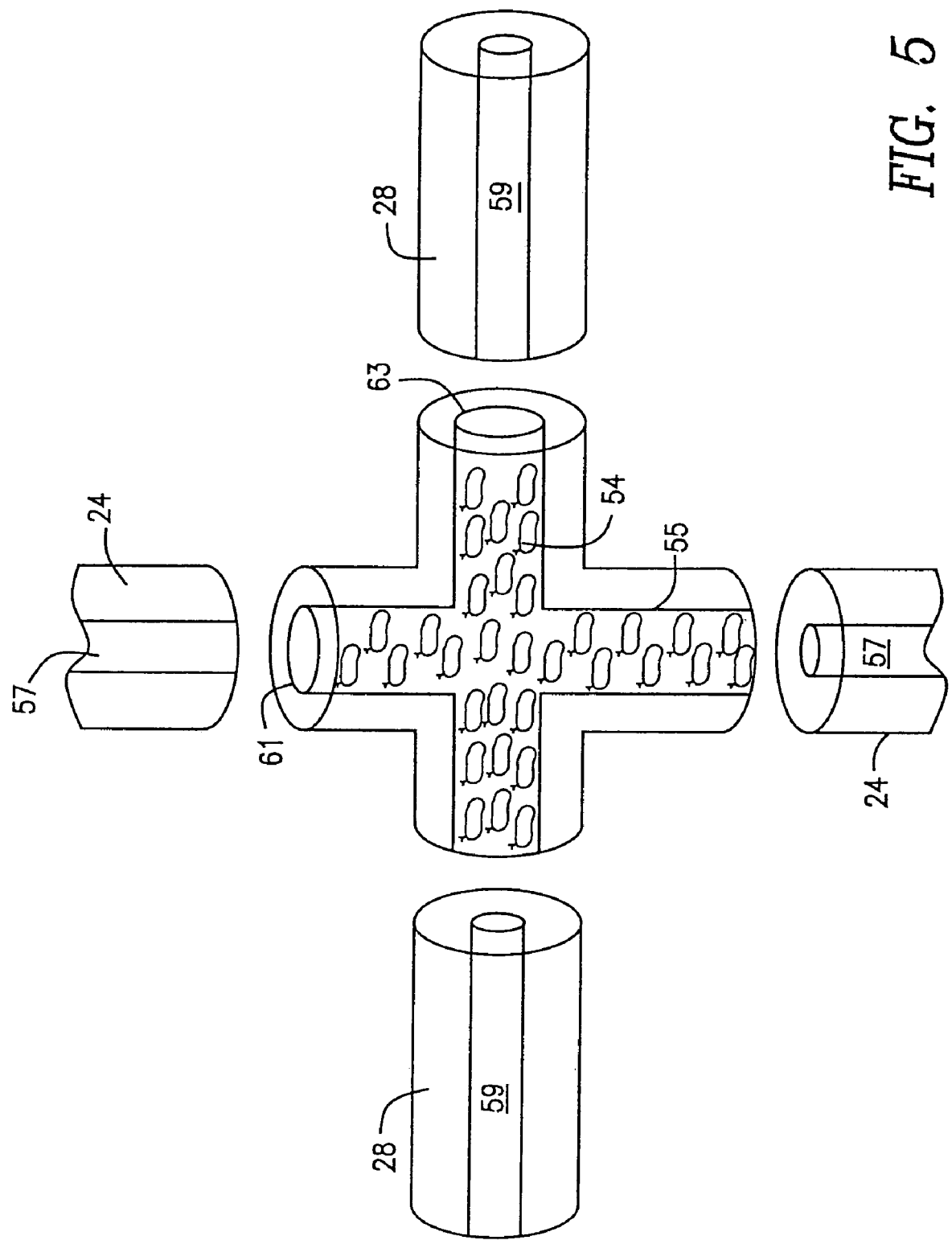
FIG. 5 is an elevated view of an analyte concentrator in the form of a cross-shaped capillary.

Alternatively, as shown in FIG. 5, analyte concentrator 55 can be fabricated by using two constricted areas with no frits at all. Analyte concentrator 55, in the form of a cross-shaped capillary, has inner diameter 61 and 63 pre-formed in relation to inner diameter 57 of transport capillary 24 and inner diameter 59 of separation capillary 28.

Analyte concentrator capillary 55 contains a plurality of previously described microstructures 54 which are larger than inner diameters 57 and 59. They are typically coated with non-specific chemistries such as C-18 or highly specific antibodies or antigens having an affinity for one of the analytes under investigation. Several other well-known chemistries can also be used.

In the embodiment illustrated by FIG. 5, microstructures 54 are retained or confined in the interior of analyte concentrator 55 by making inner diameter 57 of transport capillary 24 smaller than inner diameter 61 of analyte concentrator 55. In like manner, inner diameter 59 of separation capillary 28 is smaller than inner diameter 63 of analyte concentrator 55. For example, inner diameters 57 and 59 may be one-quarter to one-half the size of inner diameters 61 and 63.

To increase detection sensitivity for a particular analyte, a chromophore may be added to the eluting buffer to elute and tag the bound analyte for the purpose of enhancing the ultraviolet absorptivity, fluorescence, phosphorescence, chemiluminescence or bioluminescence of the analyte as it passes through detector 46.

Figure 6:
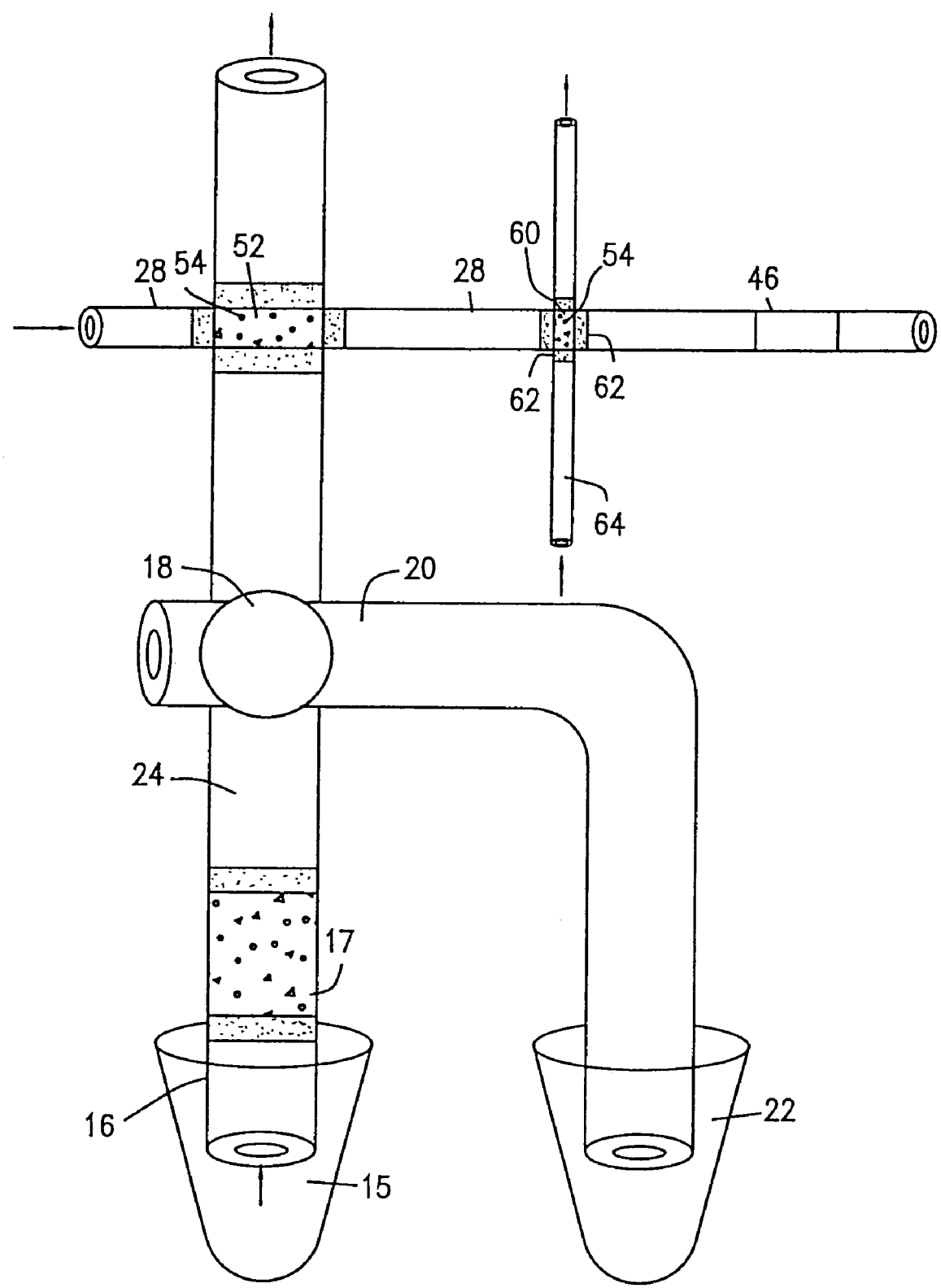
FIG. 6 is an elevated view of the electrophoresis apparatus of the present invention, showing an analyte concentrator disposed along the length of a separation capillary.

In an alternative technique to increase detection sensitivity, additional analyte concentrator 60 may be placed in one of separation capillaries 28, 30 and 32, as shown in FIG. 6. Analyte concentrator 60 has a plurality of microstructures 54 coated with a chromophoric agent or antibody that binds to a portion of a chromophoric agent which increases ultraviolet absorptivity, fluorescence or phosphorescence when bound to a minute quantity of a specific analyte. Frits 62 are located at the input and output of analyte concentrator 60, and narrow capillary 64, which intersects with separation capillary 28, carries a buffer to periodically cleanse microstructures 54 in analyte concentrator 60 after each analysis.

An analyte tagged with a chromophoric agent is more readily identified by the apparatus of the present invention, thereby increasing the sensitivity of analyte detection by as much as 100 times or more. Many different chromophoric agents emit light when they bind a specific functional group to form a product molecule in an electronically excited state.

Figure 7:
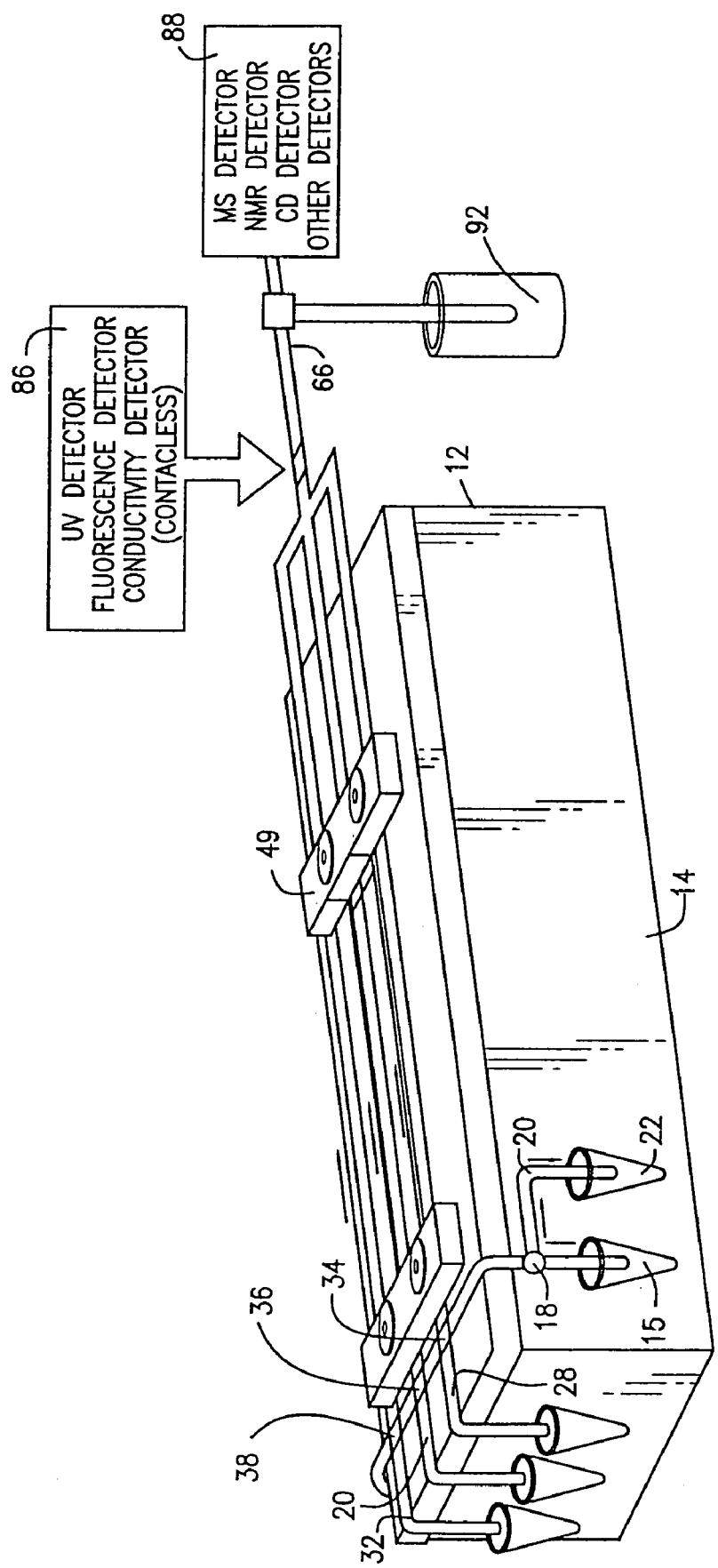
FIG. 7 is a perspective view of a third embodiment of the present invention, showing a plurality of separation capillaries connected to a single outlet capillary for sequential detection.

The alternative embodiment illustrated by FIG. 7 is similar to that shown in FIG. 1. But, the FIG. 7 embodiment is different because the output ends of separation capillaries 28, 30 and 32 are connected to each other at the interface with a single outlet capillary 66 which cooperates with on-column detector 86 that senses ultraviolet (UV) or fluorescent energy. The exit position of outlet capillary 66 may also be connected (as shown) to off-column detector 88 which comprises an electrochemical, mass spectrometry, circular dichroism detector or nuclear magnetic resonance detector.

The electrophoresis apparatus of FIG. 7 employs multiple separation capillaries or channels for sample concentration, but only one outlet capillary for sample detection. This coordinated separation by individual capillaries may be sequentially activated and controlled by well-known electronic circuitry. Like the FIG. 1 embodiment, preceding analytes are completely separated and detected before the next separation operation is activated.

Figure 8:
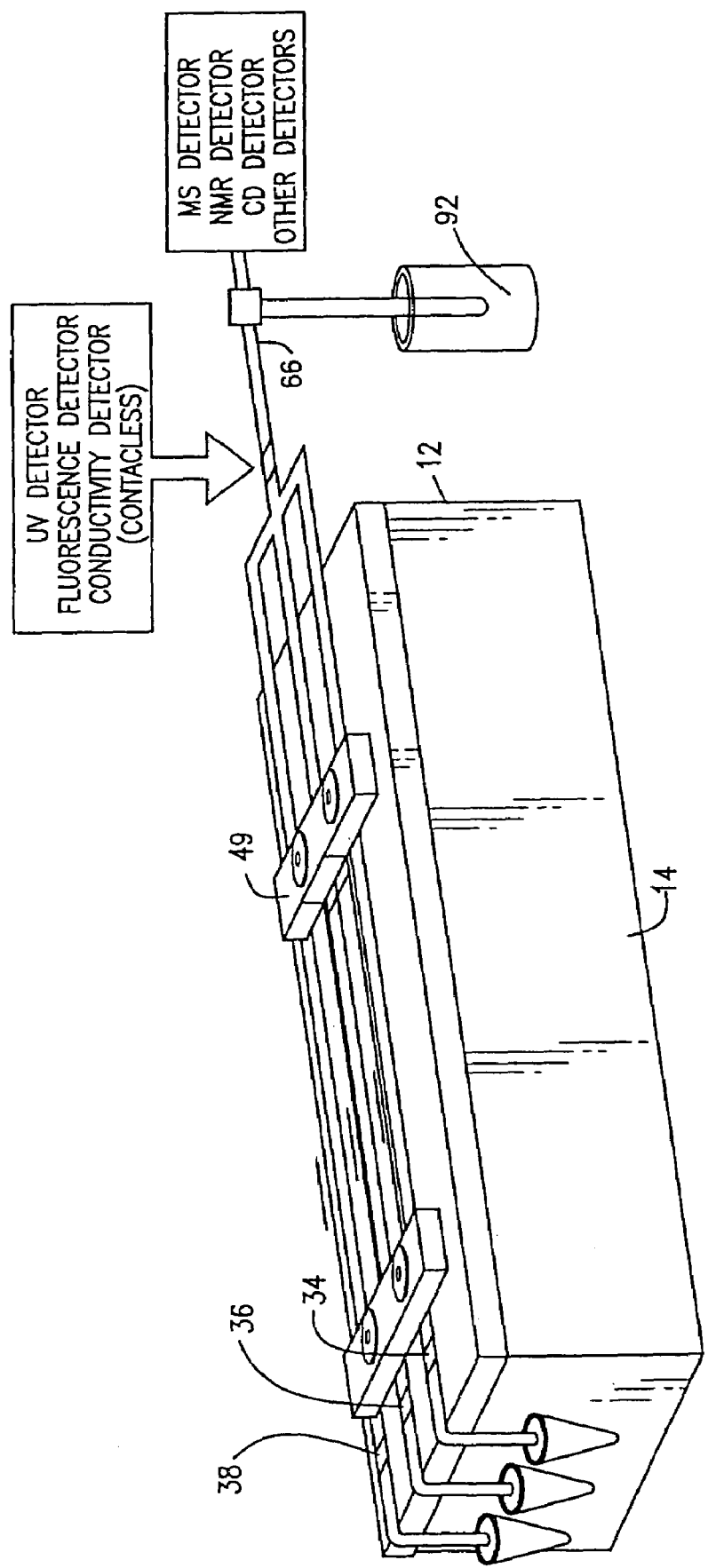
FIG. 8 is a perspective view of a fourth embodiment of the present invention, showing a plurality of separation capillaries adapted to analyze multiple samples according to the techniques described in this specification.

The electrophoresis apparatus of FIG. 8 is similar to that of FIG. 7, but it is adapted to work with multiple samples (here, e.g., three) having a simple or complex component. There is no introduction capillary 16 or sample cup 15 as provided by embodiments of FIG. 1 and FIG. 7. Separation capillaries 28, 30 and 32 are equipped with single analyte concentrators 34, 36 and 38, respectively. Individual samples are directly and sequentially delivered to separation capillaries 28, 30 and 32 and the analytes of interest are captured using suitable chemistries as previously described. The capillaries may be washed with buffer until all unwanted substances are removed. Like the FIG. 7 embodiment, separation capillaries 28, 30 and 32 are activated in series one after the other. When all the analytes are separated in a single capillary, the apparatus begins the next separation cycle. In each of the described embodiments, apparatus 10 provides greater efficiency and higher throughput when compared to prior art devices.

Various modifications and alterations to the present invention may be appreciated based on a review of this disclosure. These changes and additions are intended to be within the scope and spirit of this invention as defined by the following claims.

What is claimed is:

1. An electrophoresis apparatus, comprising:
    a transport passage having a sample inlet end and an outlet end;
    a first separation passage in fluid communication with and intersecting the transport passage at a first intersection and crossing over the transport passage;
    the first separation passage having a buffer solution inlet end;
    first affinity means for attracting and concentrating in the first intersection a first analyte of interest from a sample introduced into the transport passage and allowing the concentrated first analyte of interest to be subsequently conveyed by at least electrophoresis migration via the first separation passage to a detector system which identifies and characterizes analytes of interest;
    a second separation passage in fluid communication with and intersecting the transport passage at a second intersection which is downstream of the first intersection and crossing over the transport passage;
    the second separation passage having a buffer solution inlet end; and
    second affinity means for attracting and concentrating in the second intersection a second analyte of interest from the introduced sample and allowing the concentrated second analyte of interest to be subsequently conveyed by at least electrophoresis migration via the second separation passage to the detector system.

2. The electrophoresis apparatus of claim 1 further comprising: a third separation passage in fluid communication with and intersecting the transport passage at a third intersection which is downstream of the second intersection and crossing over the transport passage; the third separation passage having a buffer solution inlet end; and third affinity means for attracting and concentrating in the third intersection a third analyte of interest from the introduced sample and allowing the third analyte of interest to be subsequently conveyed by at least electrophoresis migration via the third separation passage to the detector system.

3. The electrophoresis apparatus of claim 2 wherein the first, second and third affinity means allow the concentrated first, second and third analytes of interest to be sequentially conveyed to the detector system.

4. The electrophoresis apparatus of claim 2 wherein the transport passage has an inner diameter larger than the inner diameters of each of the first, second and third separation passages.

5. The electrophoresis apparatus of claim 1 wherein the first affinity means includes a first matrix assembly and the second affinity means includes a second matrix assembly.

6. The electrophoresis apparatus of claim 1 wherein the first and second intersections are both cruciform-shaped intersections.

7. The electrophoresis apparatus of claim 1 further comprising a buffer solution container in fluid communication with the buffer solution inlet end of the first separation passage.

8. The electrophoresis apparatus of claim 1 wherein the buffer solution end of the first separation passage is connected to a container containing a background electrolyte, a high-viscosity solution, or an elution buffer.

9. The electrophoresis apparatus of claim 1 wherein the first separation passage allows a sample or separation buffer to be introduced thereinto by pressure, vacuum or electrokinetic flow.

10. The electrophoresis apparatus of claim 1 wherein the first affinity means includes first-analyte binding microstructures.

11. The electrophoresis apparatus of claim 10 wherein the first affinity means includes frits for holding the microstructures.

12. The electrophoresis apparatus of claim 10 wherein the microstructures are fritless microstructures.

13. The electrophoresis apparatus of claim 10 wherein the transport passage and the first separation passage include restricted diameters for retaining the microstructures.

14. The electrophoresis apparatus of claim 1 wherein the first affinity means allows the concentrated first analyte of interest to be released from the first intersection by hydrodynamically-conveyed separation buffer introduced into the buffer solution inlet end of the first separation passage.

15. The electrophoresis apparatus of claim 1 wherein the first affinity means allows the concentrated first analyte of interest to be released from the first intersection by electrokinetically-conveyed separation buffer introduced into the buffer solution inlet end of the first separation passage.

16. The electrophoresis apparatus of claim 1 wherein the first analyte of interest is adapted to be released from the first affinity means and further separated in the first separation passage by at least one of electrokinetic driven flow or hydrodynamic driven flow, or both driven flows.

17. The electrophoresis apparatus of claim 1 wherein the detector system includes a UV detector.

18. The electrophoresis apparatus of claim 1 wherein the detector system includes a fluorescence detector.

19. The electrophoresis apparatus of claim 1 wherein the detector system is an electrochemical detector.

20. The electrophoresis apparatus of claim 1 wherein the detector system is a mass spectrometer detector.

21. The electrophoresis apparatus of claim 1 wherein the detector system is a circular dichroism detector.

22. The electrophoresis apparatus of claim 1 wherein the detector system is a nuclear magnetic resonance detector.

23. The electrophoresis apparatus of claim 1 further comprising an analyte concentrator in the first separation passage and downstream of the first affinity means.

24. The electrophoresis apparatus of claim 23 wherein the analyte concentrator includes microstructures coated with a chromophoric agent to enhance ultraviolet absorptivity, fluorescence, phosphorescence, chemiluminescence or bioluminescence of the first analyte of interest passing therethrough.

25. The electrophoresis apparatus of claim 24 wherein the analyte concentrator is fritless or the microstructures are made of polymeric materials or are chemically interconnected to each other and to an inner wall of the first separation passage.

26. The electrophoresis apparatus of claim 24 wherein the analyte concentrator includes frits in the first separation passage for retaining the microstructures.

27. The electrophoresis apparatus of claim 1 further comprising an exit outlet passage into which the first and second separation passages flow, and the detector system being positioned operatively at the outlet passage.

28. The electrophoresis apparatus of claim 27 wherein each of the passages is a capillary.

29. The electrophoresis apparatus of claim 27 wherein each of the passages is a channel.

30. The electrophoresis apparatus of claim 27 further comprising: a third separation passage in fluid communication with and intersecting the transport passage at a third intersection which is downstream of the second intersection and crossing over the transport passage; the third separation passage having a buffer solution inlet end; third affinity means for attracting and concentrating in the third intersection a third analyte of interest from the introduced sample and allowing the third analyte of interest to be subsequently conveyed by at least electrophoresis migration via the third separation passage to the detector system; and the third separation passage flowing into the outlet passage.

31. The electrophoresis apparatus of claim 30 wherein the first, second and third affinity means allow the concentrated first, second and third analytes of interest to be sequentially conveyed in the outlet passage to the detector system.

32. The electrophoresis apparatus of claim 27 wherein the exit outlet passage is connected to a container having a grounding electrode.

33. The electrophoresis apparatus of claim 1 wherein an outlet end of the first separation passage and an outlet end of the second separation passage are connected to a container having a grounding electrode.

34. The electrophoresis apparatus of claim 33 wherein the first and second separation passages are connected proximate to the container to an on-line common detector.

35. The electrophoresis apparatus of claim 1 wherein the first affinity means includes microstructures carrying at least one affinity element adapted to attract the first analyte of interest.

36. The electrophoresis apparatus of claim 35 wherein the second affinity means includes microstructures carrying at least one affinity element adapted to attract the second analyte of interest.

37. The electrophoresis apparatus of claim 1 wherein the first and second separation passages are both perpendicular to the transport passage.

38. The electrophoresis apparatus of claim 1 wherein each of the passages is a capillary.

39. The electrophoresis apparatus of claim 1 wherein each of the passages is a channel.

40. The electrophoresis apparatus of claim 1 wherein the transport passage and the first and second separation passages are all formed into a microchip.

41. The electrophoresis apparatus of claim 1 further comprising a waste container into which excess amounts of sample in the transport passage pass out through the outlet end.

42. The electrophoresis apparatus of claim 41 wherein the transport passage has an inlet end in through which a washing buffer can be introduced for washing excess sample and unwanted materials out to the waste container.

* * * * *